(12) United States Patent
Hoss

(10) Patent No.: US 11,875,904 B2
(45) Date of Patent: Jan. 16, 2024

(54) IDENTIFICATION OF EPIDEMIOLOGY TRANSMISSION HOT SPOTS IN A MEDICAL FACILITY

(71) Applicant: KONINKLIJKE PHILIPS N.V., Eindhoven (NL)

(72) Inventor: Andrew G. Hoss, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 160 days.

(21) Appl. No.: 16/504,565

(22) Filed: Jul. 8, 2019

(65) Prior Publication Data

US 2019/0333647 A1 Oct. 31, 2019

Related U.S. Application Data

(60) Provisional application No. 62/695,373, filed on Jul. 9, 2018, provisional application No. 62/490,916, filed on Apr. 27, 2017.

(51) Int. Cl.
*G16H 50/80* (2018.01)
*G06N 7/01* (2023.01)
(Continued)

(52) U.S. Cl.
CPC ............... *G16H 50/80* (2018.01); *G06N 7/01* (2023.01); *G06T 15/06* (2013.01); *G16H 40/20* (2018.01);
(Continued)

(58) Field of Classification Search
CPC .......... G06F 19/00; G06F 30/20; G06F 30/13; G06N 7/005; G06N 20/00; G06Q 10/06;
(Continued)

(56) References Cited

U.S. PATENT DOCUMENTS 7,443,303 B2 * 10/2008 Spear ..................... G06Q 10/06
340/573.1
8,954,297 B2 * 2/2015 Teller ..................... G06N 20/00
703/1

(Continued)

OTHER PUBLICATIONS

Nice et al., "Investigating the impact of architectural planning and functional program on the indoor microbiome. A health concern", 2016, 4th International Conference of Indoor Air Quality and Climate (Year: 2016).*

(Continued)

*Primary Examiner* — Jonathan Ng
*Assistant Examiner* — Hunter J Rasnic

(57) ABSTRACT

In an epidemiology transmission probability analysis for a medical facility, ray origin points are distributed over a medical facility floor map. Rays are cast from the ray origin points. The cast rays stop upon encountering a physical barrier mapped in the medical facility floor map. An infectious transmission probability map is computed from intersections of the cast rays. At least a portion of the medical facility floor map is displayed on a display, overlaid with the infectious transmission probability map. The distributing, the casting, and the computing are suitably performed by one or more electronic processors.

26 Claims, 7 Drawing Sheets

(51) Int. Cl.
*G06F 30/13* (2020.01)
*G16H 40/20* (2018.01)
*G16H 50/30* (2018.01)
*G16H 70/60* (2018.01)
*G06N 20/00* (2019.01)
*G06Q 10/06* (2023.01)
*G06F 30/20* (2020.01)
*G06T 15/06* (2011.01)

(52) U.S. Cl.
CPC ............ *G16H 70/60* (2018.01); *G06F 30/13* (2020.01); *G06F 30/20* (2020.01); *G06N 20/00* (2019.01); *G06Q 10/06* (2013.01); *G06T 2210/04* (2013.01); *G16H 50/30* (2018.01)

(58) Field of Classification Search
CPC .......... G06Q 10/063114; G06T 15/005; G06T 15/06; G06T 17/05; G06T 2210/04; G16H 40/20; G16H 50/80; G16H 70/60; G16H 50/30
See application file for complete search history.

(56) References Cited

U.S. PATENT DOCUMENTS

| | | | | |
|---|---|---|---|---|
| 2005/0081161 A1* | 4/2005 | MacInnes | ............... | G06K 9/00 715/765 |
| 2010/0332022 A1* | 12/2010 | Wegelin | ............... | G16H 40/20 715/764 |
| 2011/0131054 A1* | 6/2011 | Theobald | ............... | G16H 40/20 705/2 |
| 2011/0191069 A1* | 8/2011 | Madsen | ................ | G06F 30/13 703/1 |
| 2013/0318027 A1* | 11/2013 | Almogy | ............... | G16H 50/20 706/52 |
| 2014/0163928 A1* | 6/2014 | Kalai | ............ | G06F 30/00 703/1 |
| 2014/0167917 A2* | 6/2014 | Wallace | ............... | G16H 40/67 340/10.1 |
| 2014/0257779 A1* | 9/2014 | Yoon | .............. | G06T 13/40 703/6 |
| 2015/0123971 A1* | 5/2015 | Lee | ............ | G06T 15/06 345/426 |
| 2015/0213225 A1* | 7/2015 | Amarasingham | ....... | G06F 19/00 705/2 |
| 2015/0227645 A1* | 8/2015 | Childs | ................. | G06F 30/13 703/1 |
| 2015/0278456 A1* | 10/2015 | Bermudez Rodriguez | ............ | G06F 19/00 705/2 |
| 2016/0093194 A1* | 3/2016 | Herzog | ............... | G16H 40/20 340/573.1 |
| 2016/0132652 A1* | 5/2016 | Chapman Bates | .... | G16H 50/20 706/11 |
| 2016/0188755 A1* | 6/2016 | Gonzalez-Banos | ..... | G06F 30/20 703/1 |
| 2016/0217225 A1* | 7/2016 | Bell | ................ | G06F 30/13 |
| 2016/0306934 A1* | 10/2016 | Sperry | ................. | G06F 3/147 |
| 2016/0337888 A1* | 11/2016 | Zhang | ................ | G06T 17/05 |
| 2017/0024531 A1* | 1/2017 | Malaviya | ............... | G16H 40/63 |
| 2020/0126662 A1* | 4/2020 | Li | ................ | G16H 50/20 |

OTHER PUBLICATIONS

Sathik et al., "Ray Casting for 3D Rendering—A Review", Feb. 1, 2015, International Journal of Innovations in Engineering and Technology (IJIET), vol. 5 (Year: 2015).*

Ray et al., "Ray Casting Architectures for Volume Visualization", Apr. 1999, Mitsubishi Electric Research Laboratories Inc. (Year: 1999).*

Frandsen, et al., "Spatial configurations of healthcare practices", pp. 1062-1973 (Abstract).

Nice, et al., "Investigating the impact of architectural planning and functional program on the indoor microbiome. A health concern", 8 pages. (Abstract).

Taylor, et al., "Human Factors and Bioagent Transmission Following an Indoor Bioterror Attack", Journal of Bioterrorism & Biodefense 2012, vol. 3, Issue 1, pp. 1-8.

Sailer, et al., "Paths of reistant pathogens in hospitals: architecture, design interventions, transmission risks", 3 pages. (Abstract).

Neo, et al., "The Influence of spatial configuration on the frequency of use of hand sanitizing stations in health care environments", American Journal of Infection Control 2017, 5 pages.

* cited by examiner

IDENTIFICATION OF EPIDEMIOLOGY TRANSMISSION HOT SPOTS IN A MEDICAL FACILITY

CROSS-REFERENCE TO RELATED APPLICATIONS

The present application claims priority to and the benefit of both U.S. Provisional Application Ser. No. 62/695,373, filed Jul. 9, 2018, and U.S. Provisional Application Ser. No. 62/490,916, filed Apr. 27, 2017, which are hereby incorporated by reference herein.

FIELD

The following relates generally to the epidemiology arts, hospital planning arts, patient care arts, medical facility construction arts, and related arts.

BACKGROUND

The occurrence of hospital patients acquiring infections during hospital stays is sufficiently common that the acronym "HAI" (standing for "hospital-acquired infection" or "healthcare-acquired infection") has come into common usage in the medical community. Infectious transmission can occur by various modes, e.g. airborne transmission, droplet transmission (e.g. during coughing or the like), direct contact with an infected person, or surface-mediated transmission (e.g. touching a door handle or other surface previously contacted by an infected person). A given infectious agent causing HAIs may be transmissible only by certain transmission modes. Airborne or droplet-mediated transmission mechanisms are particularly insidious as they can act over a distance without direct contact with any person or surface.

When an HAI outbreak occurs in a hospital, extensive resources are required to track the transmission vectors, and identify, isolate, and treat infected persons. The HAI outbreak leads to increased medical costs and patient illnesses or even deaths. Thus, prevention of HAI transmission is preferable. But prevention is a challenging task, especially in the case of airborne or droplet transmission. The latency time between transmission of the infectious agent and onset of symptoms can make determination of the infectious pathways difficult or impossible.

The following discloses certain improvements.

SUMMARY

In some embodiments disclosed herein, a non-transitory computer readable medium has stored thereon program code readable and executable by one or more electronic processors operatively connected with at least one display to perform operations including: distributing ray origin points over a medical facility floor map; casting rays from the ray origin points, the cast rays stopping upon encountering a physical barrier mapped in the medical facility floor map; generating an infectious transmission probability map from intersections of the cast rays over the medical facility floor map; and displaying, on the at least one display, at least a portion of the medical facility floor map overlaid with the infectious transmission probability map.

In some embodiments disclosed herein, a method of epidemiology transmission probability analysis is disclosed. Ray origin points are distributed over a medical facility floor map. Rays are cast from the ray origin points. The cast rays stop upon encountering a physical barrier mapped in the medical facility floor map. An infectious transmission probability map is generated from intersections of the cast rays. At least a portion of the medical facility floor map is displayed on a display, overlaid with the infectious transmission probability map. The distributing, the casting, and the computing are suitably performed by one or more electronic processors.

In some embodiments disclosed herein, an epidemiology transmission probability analysis device is disclosed, comprising at least one electronic processor, at least one display operatively connected with the electronic processor, and at least one non-transitory storage medium storing a medical facility floor map and instructions. The instructions are readable and executable by the at least one electronic processor to perform operations including: distributing ray origin points over the medical facility floor map; casting rays from the ray origin points, the cast rays stopping upon encountering a physical barrier mapped in the medical facility floor map; generating an infectious transmission probability map from intersections of the cast rays; computing an infectious transmission probability for a space or transport route of the medical facility floor map by aggregating the spatially dependent infectious transmission probability given by the infectious transmission probability map over the space or transport route; and controlling the at least one display to present at least a portion of the medical facility floor map overlaid with a graphic representing the space or transport route with the graphic labeled with the computed infectious transmission probability for a space or transport route.

One advantage resides in providing automated identification of infectious transmission hotspots (i.e. locations with high probability of transmission of an HAI) of a hospital or other medical facility.

Another advantage resides in providing such automated identification of infectious transmission hotspots with high computational efficiency.

Another advantage resides in providing such automated identification of infectious transmission hotspots which accounts for physical barriers to transmission.

Another advantage resides in providing such automated identification of infectious transmission hotspots which accounts for the transmission zone of a specific HAI and/or specific modality of transmission (e.g. airborne, droplet-borne, contact, and/or et cetera).

Another advantage resides in providing a patient routing system with automated identification of infectious transmission hotspots to be avoided for critically ill patients.

Another advantage resides in providing a hospital cleaning schedule optimizer with automated identification of infectious transmission hotspots.

Another advantage resides in providing a hospital floor-plan optimizer with automated identification of infectious transmission hotspots.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 1 diagrammatically illustrates a device for mapping probability of infectious transmission in a hospital or other medical facility, in conjunction with various applications using such an HAI transmission (HAIx) probability hospital floor map (illustrative applications including a patient transport router, a hospital cleaning scheduler, and a hospital floorplan designer).

DETAILED DESCRIPTION

Figure 1:
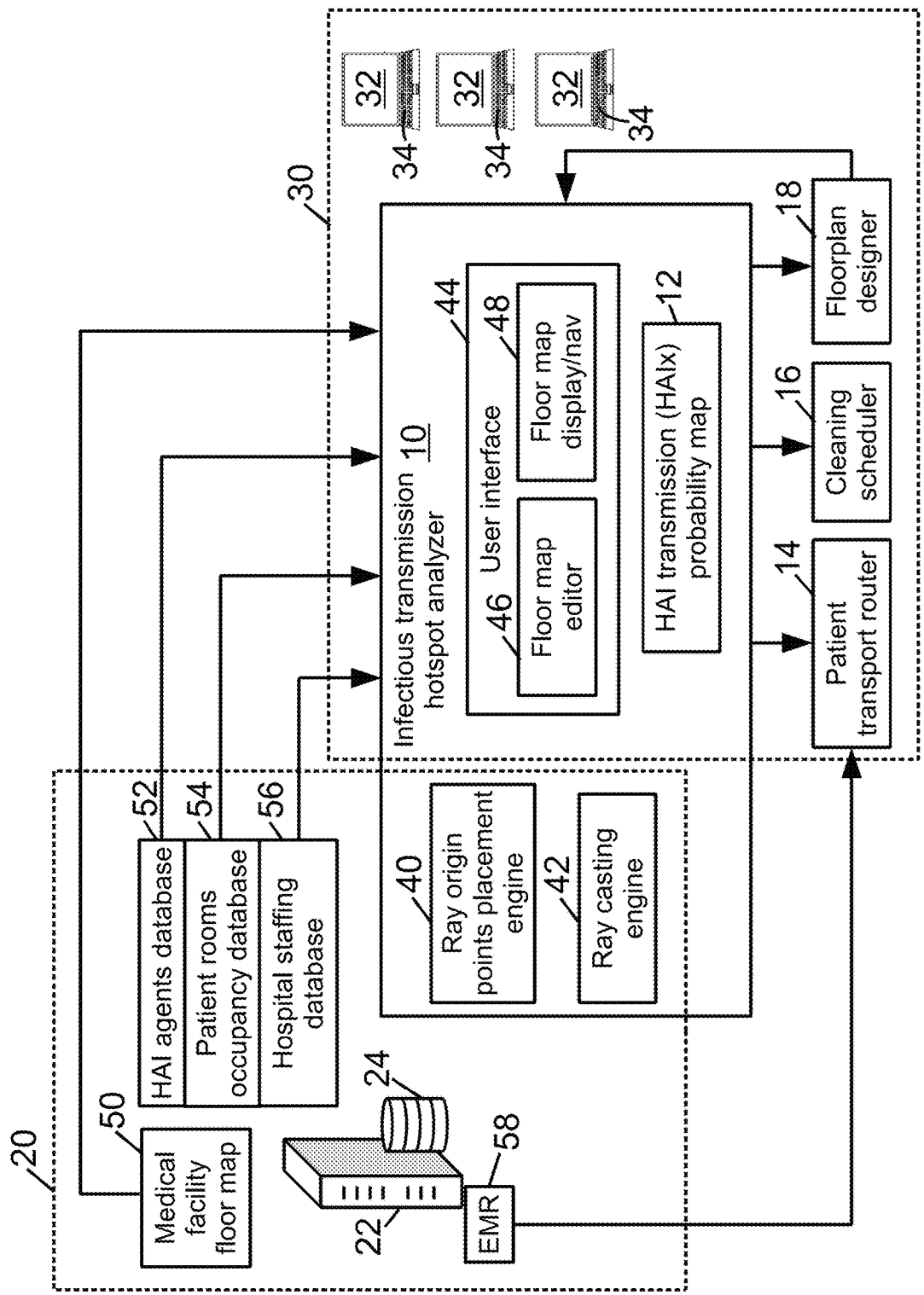

For hospital epidemiology, location over time is essential in understanding the potential route of transmission of an infection or outbreak during a given timeframe. To perform such investigations, records are directly accessed and manually matched. Cartesian coordinate (e.g., X,Y,Z) mapping of floor plans extracted from blueprints can be stored in an encrypted linkage format to infer patient-patient interaction from information provided by a real-time locating service (RTLS, e.g. RFID tag-reader station based or otherwise implemented). However, coordinates-based matching for epidemiology analysis poses a challenge, as distances in the Cartesian space do not reflect actual spatial relationships when factors such as barriers (doors, wall, or so forth), constrictions (e.g. a hallway that variously narrows and widens along its length) are taken into account. For example, the existence of a wall between two points may preclude infectious transmission between the two points even though they may be within the infectious transmission distance for the transmission modality of the HAI.

More complex analyses could be envisioned, for example using Cartesian mapping subject to a series of constraints embodying all walls and other barriers present. However, such analysis would be computationally complex, and each barrier would need to be translated into an appropriate constraint.

Furthermore, transmission probabilities are not solely dependent on Cartesian distances and physical barriers. Rather, transmission probabilities are also dependent upon other factors such as typical occupancy of spaces. As an example, consider transmission probability between two points that are spaced apart by a certain distance with no intervening physical barriers. The transmission probability is higher if those two points are both located in the center of a medical ward with a high density of patients and medical personnel, as compared with if those two points are both located inside of a closet that is infrequently accessed by cleaning personnel. Incorporating such factors into a constrained Cartesian analysis would further complicate the already complex constrained Cartesian mapping.

Infectious transmission hotspot analysis embodiments disclosed herein overcome the foregoing difficulties by using a ray casting approach. Multiple points are placed across the floor map (e.g., at random). Then, for each point, a number of rays are cast outward (e.g., in random directions), and each ray extends until it hits a boundary. The number of rays may be selected based on factors such as, e.g., the statistical occupancy of each space (e.g., more rays for points located in a waiting room as compared with points located in a patient bedroom) or the communicability of a specific disease being mapped (e.g., more rays for more infectious diseases). Optionally, each cast ray may have a maximum length dictated by size of the infectious zone of the specific disease being mapped, e.g. if the infectious zone has a size of three meters then a ray is terminated either when it reaches a barrier (e.g. wall) or when it reaches the maximum length of (in this case) three meters, whichever distance is shorter. Once all rays have been cast, the floor map is displayed, color coded based on the number of ray intersections at a given point. More ray intersections are interpreted as a "hotter" pixel on the map, thus indicating a higher degree of communicability based on patient traffic through the area.

The disclosed ray casting approaches for mapping HAI transmission (also represented herein by the shorthand "HAIx") probability over the area of a floor of a hospital or other medical facility has substantial advantages. It can be applied directly to the floor map without requiring a user to abstract out constraints to represent walls or other barriers. The use of cast ray intersections to capture data on HAIx probability provides a computationally efficient and intuitive way to capture the complexities of infectious transmission likelihood in real spaces. For example, the ray casting approach naturally captures the expectation that HAIx is most likely in the central area of a room or other open space where persons are likely to come into close proximity or possible contact; whereas, HAIx is less likely in the case of a person near a wall defining such a space since that person is away from the usual central pathway of traffic. Likewise, a point in a patient room extending off a central hallway will have fewer ray intersections than a point in that hallway, accurately reflecting the lower likelihood of HAIx involving a person in the relatively isolated patient room compared with a person in the more heavily traveled hallway. It is straightforward for a user to introduce virtual barriers to represent circumstances or building features that prevent or reduce likelihood of transmission, such as a restricted area that is restricted by access-limiting signage (e.g. a "Do not enter" sign) but not by any wall, door, or other physical barrier. Porous physical barriers, that is, physical barriers that hamper but do not completely prevent infectious transmission (e.g. a door that is usually closed but may be open, or an area that is restricted by signage but which may be entered in contravention to the signage) can be captured in the ray casting approach by a probabilistic likelihood that a ray is stopped by the barrier, where the probability of ray stoppage represents the porosity of the porous physical barrier. Likewise, the ray casting approach can readily capture aspects such as the infectious zone size (by setting a maximum permissible ray cast length), statistical occupancies of various spaces (captured by the number of rays cast), and so forth. The complexities of an HAI with multiple transmission pathways (e.g. airborne or by contact) can be similarly intuitively captured. For example, if the likelihood of airborne transmission is 30% and the likelihood of contact transmission is 70% then this can be captured by using 30% of the cast rays having maximum permissible length equal to the airborne transmission infectious zone size and 70% of the cast rays having maximum permissible length equal to the contact transmission infectious zone size. The disclosed ray casting approaches for mapping HAIx probabilities also advantageously automatically generates a two-dimensional map of HAIx probabilities. For example, the floor plan can be color coded by the number of intersections per voxel, with higher number of intersections being interpreted as a higher HAIx probability.

With reference to FIG. 1, an illustrative infectious transmission hotspot analyzer device 10 is described for generating an HAI transmission (HAIx) probability map (more generally, infectious transmission probability map) 12, along with various illustrative applications suitably using the HAIx probability map 12 such as an illustrative patient transport router 14, an illustrative hospital cleaning scheduler 16, and an illustrative hospital floorplan designer 18. These components may be variously implemented. In the illustrative example of FIG. 1, implementation is by way of: a server computer or computer cluster or cloud computing resource 20 including at least one server computer 22 and at least one non-transitory storage medium 24 operatively connected with the at least one server 22; and one or more local computers 30 each including and/or having operative access to non-transitory storage media (not shown), at least one display 32 and a keyboard, mouse, touch-sensitive display, or other user input device 34. The one or more computers and/or computing resources 20, 30 are understood to comprise one or more electronic processors (e.g. microprocessors), and the non-transitory storage medium or media my, by way of non-limiting illustrative example, comprise one or more of: a hard disk drive or other magnetic storage medium; a solid state drive (SSD), flash memory, read-only memory (ROM), erasable programmable ROM (EPROM), or other electronic storage medium; an optical disk or other optical storage medium; various combinations thereof, and/or so forth. In a typical architecture, the server computer or computer cluster or cloud computing resource 20 has substantial computing capacity and speed and is used to perform computationally intensive operations such as implementing ray origin points placement engine 40 and ray casting engine 42 components of the illustrative infectious transmission hotspot analyzer device 10, while the one or more local computers 30 implement a user interface 44 of the illustrative infectious transmission hotspot analyzer device 10, for example providing: a floor map editor 46 via which a user can load medical facility floor map 50, overlay occupancy information or the like, and edit the map to add virtual barriers, delineate non-absolute barriers, and/or so forth; and a floor map display/navigation engine 48 via which a user can display and scroll through the HAIx probability floor map 12, e.g. by overlaying the HAIx probability map 12 via color coding or the like onto the electronic medical facility floor map 50, and perform various analyses. However, the infectious transmission hotspot analyzer device 10 and its various components 40, 42, 44 may be otherwise implemented, e.g. a local computer may implement the entire infectious transmission hotspot analyzer device 10 including the more computationally demanding components 40, 42 if it has sufficient computing capacity.

The server computer or computer cluster or cloud computing resource 20 also typically stores or has access to various data sources, some illustrative examples of which are diagrammatically shown in FIG. 1. A stored electronic medical facility floor map 50 stores a Cartesian coordinate (e.g., X,Y,Z) mapping of floor plans for the hospital or other medical facility extracted from (electronic) architectural blueprints of the building and buildout information for the various floors of the medical facility. The electronic medical facility floor map 50 is typically (though not necessarily) a data source that is already available for use by a real-time locating service (RTLS), and/or by hospital security, and/or by hospital emergency response personnel, and/or for other uses, and is leveraged by the infectious transmission hotspot analyzer 10. An illustrative HAI agents database 52 stores information about known HAI agents, such as agent identification (viral or bacterial and information on the specific biological agent), modes of infectious transmission including transmission zone size information, qualitative and/or quantitative metrics of communicability (e.g. highly infectious, infection rate of xx% via airborne transmission, et cetera), diagnostic guidance, quarantine guidance and treatment options, and/or so forth. Again, this information is typically (though not necessarily) a data source that is already available for use by hospital emergency response personnel or the like. Further data sources 54, 56 provide information on statistical occupancies of various rooms or other spaces of the hospital. For example, a patient rooms occupancy database 54 may store information on the occupancy rates of hospital beds in various wings, wards, or the like of the hospital, and may be constructed from in-patient admissions data or the like. A hospital staffing database 56 stores information on staff allocations, e.g. the number of staff assigned to various areas. From such data sources 54, 56 the statistical occupancy of various spaces of the hospital can be estimated. Still further, the server computer or computer cluster or cloud computing resource 20 may store or have access to patient data, e.g. an Electronic Medical Record (EMR) 58. This is merely an example, and the patient data may be stored in an otherwise-named electronic database such as an Electronic Health Record (EHR), and/or a domain-specific database such as a radiology information system (RIS), cardiovascular information system (CVIS), and/or the like. These patient data resources 58 store information on specific patients, from which de-identified aggregate data optionally may be extracted.

With continuing reference to FIG. 1 and further reference to FIGS. 2-7, some illustrative embodiments of a method of epidemiology transmission probability analysis suitably implemented by the infectious transmission hotspot analyzer device 10 which generates the HAIx probability hospital map 12 and various applications using this map 12, such as the illustrative patient transport router 14, hospital cleaning scheduler 16, and hospital floorplan designer 18, are next described.

Figure 2:
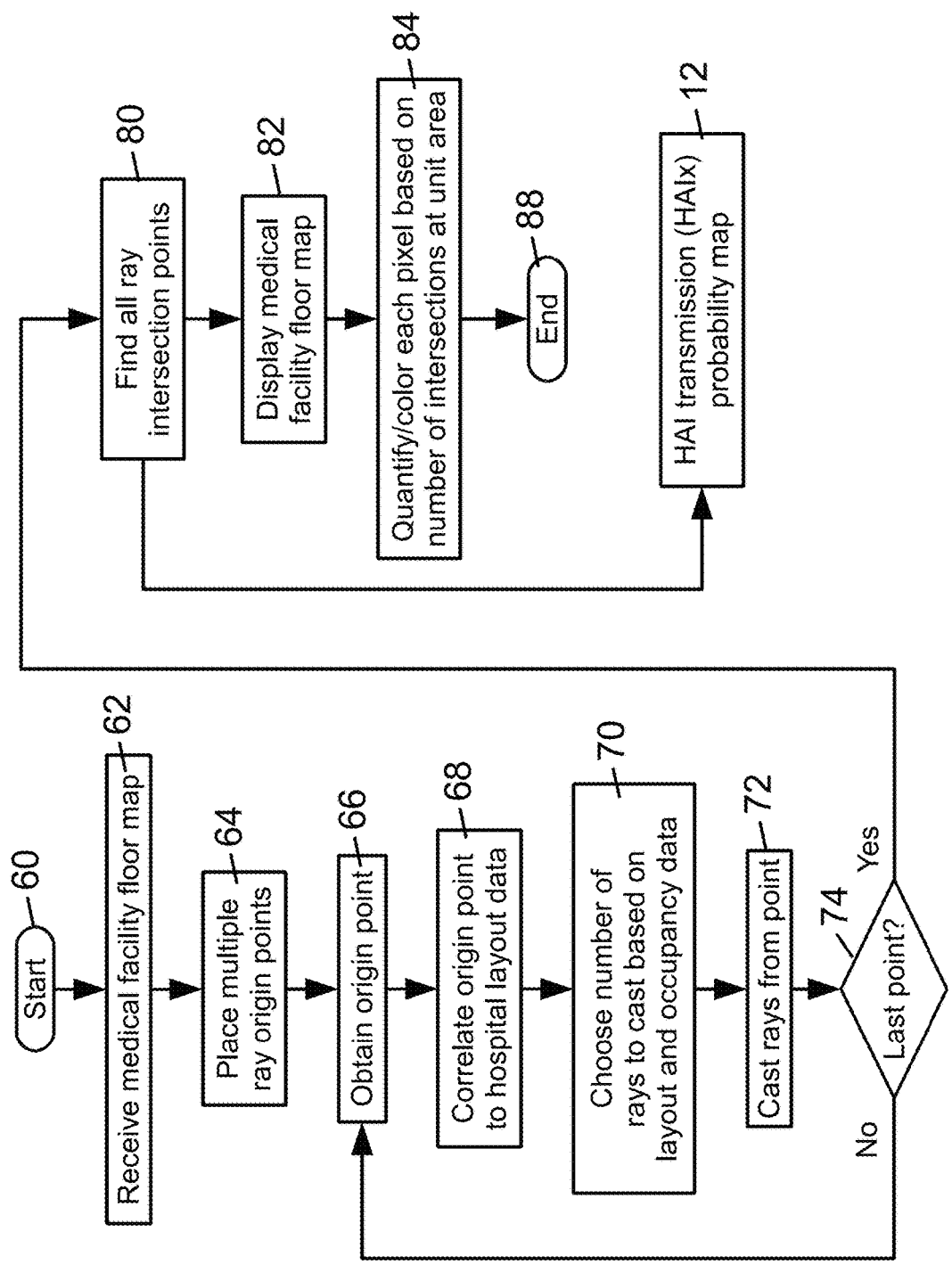
FIG. 2 diagrammatically shows operation of an illustrative embodiment of the infectious transmission hotspot analyzer of FIG. 1.

With reference to FIG. 2, in a suitable embodiment the infectious transmission hotspot analyzer device 10 generates the infectious transmission probability map 12 as follows. The process starts at 60. In an operation 62, the medical facility floor map 50 is retrieved from an electronic data storage or otherwise received. In an operation 64, the ray origin points placement engine 40 (see FIG. 1) places multiple ray origin points distributed over the medical facility floor map 50. In one approach, the operation 64 places the origin points with a uniform random (or pseudo-random) distribution over the areas of the floor map 50. Alternatively, the distribution of the placed origin points can be chosen based on prior information. For example, if occupancy statistics for the medical facility are provided to the analyzer device 10 (e.g., obtained from the patient rooms occupancy database 54 and/or the hospital staffing database 56 in the example of FIG. 1), then the distribution of the ray origin points may be chosen to be dependent on the occupancy statistics for the medical facility where the origin points reside, e.g. areas with higher occupancy density will have a proportionately higher density of origin points. It will be appreciated that a higher density of origin points will (all else being equal) result in a higher number of cast ray crossings, and hence this choice of distribution of the origin points will effectively capture the greater HAIx probability due to higher occupancy density.

In a variant approach, spaces of the medical facility floor map 50 may be classified in accord with a set of space classifications. For certain purposes, such as in this example, the medical facility floor map 50 may be divided into spaces. A space is a contiguous area of the floor map having some delineated boundaries. Typically, a space corresponds to a room of the floor map 50, which is delineated by walls and one or more doorways. However, other types of spaces may be defined. For example, a waiting room may be divided into a receptionist's space or a front desk space where hospital personnel are stationed, and a waiting area space where patients wait. Similarly, a critical care ward may include spaces such as a nurses' station space where central patient monitors and/or workstations are located, patient room spaces corresponding to patient rooms, and one or more hallway spaces corresponding to one or more hallways connecting with the patient rooms and the nurses' station. There may also be stairway spaces or elevator spaces that correspond to stairways or elevators, respectively, that connect different floors. These are merely non-limiting illustrative examples. In this variant approach, estimates of the occupancy statistics may be inferred from the space classifications, e.g. a space classified as a common area or as a hallway is likely to have higher occupancy density than a space classified as a closet or storage area, for example. Hence, the distribution of the ray origin points placed at operation 64 may be dependent on the space classifications of the spaces of the medical facility floor map 50 in which the origin points reside (i.e. are placed), with a higher density of origin points being placed in spaces classified as common areas or hallways or so forth with typically high occupancy densities, and a lower density of origin points being placed in spaces classified as closets or storage or so forth with typically low occupancy densities.

With continuing reference to FIG. 2, the ray casting is performed, with each ray cast from one of the origin points placed at operation 64. To this end, in an operation 66 a (first) origin point is obtained or selected, and in an operation 68 this origin point is correlated to the hospital layout data (that is, its location in the medical facility floor map 50 is obtained—typically, each origin point is stored with its coordinates in the floor map 50 so this correlation is straightforward). In an operation 70, the number of rays to cast from the origin point selected at 66 is chosen. Various approaches may be used. In one approach, the number of rays cast from each origin point is fixed (e.g., N=200 rays cast per origin point, or more generally some other value for N may be chosen; in illustrative FIG. 3 the choice N=4 is used for illustrative purposes, but typically N will be much higher so that the number of ray crossings provides useful statistics). Alternatively, the number of rays cast from each origin can be chosen differently for different origin points, based on prior information. For example, if occupancy statistics 54, 56 for the medical facility are provided to the analyzer device 10 then the number of rays cast from each origin point may be chosen to be dependent on the occupancy statistics for the medical facility where the origin point resides, e.g. an origin point in an area with higher occupancy density will have a proportionately higher number of cast rays. In a variant approach, the number of rays cast from each origin point depends on the classification of the space of the medical facility floor map 50 in which the origin point resides. It will be appreciated that a higher number of rays cast from an origin point will (all else being equal) result in a higher number of cast ray crossings proximate to that origin point, and hence this choice of number of cast rays will effectively capture the greater HAIx probability due to higher occupancy density (or space of classification typically corresponding to higher occupancy density).

As noted above, it is contemplated to use prior information such as occupancy statistics or space classifications in choosing the distribution for placement of origin points at operation 64, or to use such prior information in choosing the number of rays to cast from each origin point at operation 70. Typically, the prior information will be captured in only one of these two operations 64, 70, although different types of prior information may be captured using each approach. For example, the space classifications may be used to control the distribution of origin points in operation 64, and then occupancy statistics may be used to adjust the number of cast rays per origin point in operation 70 to capture occupancy density differences within a given space classifications (e.g. some hallways may see more traffic than other hallways).

As another illustrative approach, one of the operations 64, 70 may be adjusted based on occupancy statistics or space classifications as discussed above, and the other of the operations 64, 70 may be adjusted based on patient population characteristics such as infection rate or susceptibility to infection. As an example of this variant, the operation 64 may distribute the origin points on the basis of occupancy statistics (possibly inferred from space classifications). Then, the number of rays cast from each origin point in operation 70 may be chosen based on patient population characteristics, e.g. origin points in a pediatric ward or a critical care ward may have more cast rays per origin point than origin points in a visitors' waiting area, so as to reflect the higher susceptibility to contracting an HAI by young patients or critically ill patients as compared with visitors who are typically healthy adults.

In an operation 72, the number of rays chosen at operation 70 are cast from the origin point chosen at the operation 66. The rays are suitably cast at equal angular intervals around the origin point, e.g. if N rays are cast then the rays are cast at 360°/N angular intervals (i.e. 360°/N angular distances between angularly adjacent cast rays). The cast rays stop upon encountering a physical barrier (e.g. a wall) mapped in the medical facility floor map 50. Other stopping criteria may be applied during the ray casting. For example, if a virtual barrier is defined in the medical facility floor map, then cast rays further stop upon encountering the virtual barrier. Optionally, a maximum ray length can be chosen and a cast ray then stops if it reaches this maximum ray length. As an example, if the infectious transmission hotspot analyzer 10 is performing epidemiology transmission probability analysis for a particular infectious agent having a known infectious transmission zone size, then the maximum ray length can be set to this zone size and the cast rays stop upon the cast ray reaching a length equal to the infectious transmission zone size. The cast ray stops upon first reaching a stopping criteria, e.g. in the foregoing example the cast ray extends until it reaches a physical (or virtual) barrier or until it reaches its maximum ray length, whichever occurs first. The cast rays may be of a chosen height or range of heights. For example a Visibility Graph Analysis (VGA) investigates the properties of a visibility graph derived from a spatial environment. Typically, a VGA is applied at eye level for what people can see, and/or at knee level as barriers at knee level impact walking mobility. The infectious transmission hotspot analyzer 10 generates the infectious transmission probability map 12 from densities of intersections of the cast rays over the medical facility floor map. This is not directly related to visibility or walking mobility since in some instances an infectious disease can transmit across barriers that may not impede vision or movement, e.g. via airborne transmission. Nonetheless, performing the ray-casting operation 72 for rays at eye level (for example, 5.5 feet above the floor, although a higher or "standard" value for eye level can be chosen, e.g. selected based on the average height of the local population) and/or knee level (for example, 1.5 feet above the floor, although again a higher or "standard" value for knee level can be chosen) is useful as such ray casting effectively simulates visibility and walking mobility, respectively, and in practice human movements are typically along visually perceived clear paths (simulated by rays cast at eye level) and along pathways that are clear of barriers at knee level. A combination of rays cast at eye level and at knee level is contemplated in order to simulate both types of human movement factors.

It is also contemplated to have a barrier with probabilistic stopping criteria, e.g. at least one physical barrier mapped in the medical facility floor map 50 (or, alternatively, a defined virtual barrier) may be mapped (or defined) as a porous physical (or virtual) barrier, and the cast rays stop upon encountering the porous barrier with a stopping probability indicative of porosity of the porous barrier. This may be useful to represent a barrier that hinders, but does not fully prevent, passage through the barrier. For example, while no one can pass through a wall, patients and/or hospital staff may pass through a doorway but with some hindrance. This may be physical hindrance in that the door must be opened to pass; and/or may be sociological hindrance in that it is generally considered inappropriate to enter a patient room without invitation or some appropriate reason such as providing nursing care. Hence, the doorway may be represented as a porous barrier with some stopping probability indicative of the amount of hindrance it presents. By stopping upon encountering the porous barrier "with a stopping probability", it is meant that the probability that the ray stops at the porous barrier is given by the stopping probability—for example, if the porous barrier has a 30% stopping probability then 30% of the rays that intersect the porous barrier stop at the porous barrier while 70% of the rays pass through the porous barrier. This approach captures (in a statistical sense) the impact of the hindrance presented by the porous barrier on HAIx probability across the porous barrier.

The ray casting 72 may be performed using any suitable ray casting algorithm, such as ray casting algorithms commonly used in computer graphics rendering to determine the line of sight from the vantage point of an observer (corresponding to the origin point described above) in a mapped two-dimensional (2D) or three-dimensional (3D) space (corresponding to the medical facility floor map 50 in the present application). The ray casting is applied starting at the origin point chosen at 66 and extends until a stopping criterion is met (e.g. intersecting a physical or virtual barrier, optionally stopping with a specified probability in the case of a porous barrier; or when it reaches a specified maximum ray length, whichever comes first). At 74, it is determined whether ray casting has been performed at all origin points: if not, then flow passes back to operation 66 to obtain the (next) origin point at which to perform ray casting.

When, at the operation 74, it is determined that ray casting has been performed at all origin points placed at the operation 64, flow passes to the HAIx probability mapping. At an operation 80, all cast ray intersection points are identified. The density of ray intersection points is taken as a metric of the HAIx probability, and hence the number of ray intersection points per unit area is determined to generate the HAI transmission (HAIx) probability map 12. The unit area used in generating the HAIx probability map 12 may be the voxels of the medical facility floor map 50, or alternatively a coarser-resolution area unit may be used in generating the HAIx probability map 12. In general, the number of origin points distributed at 64 and the number of rays cast per origin point chosen at 70 should be high enough to provide a statistically significant number of ray intersections for providing the HAIx probability map 12 with the desired area unit size (i.e. resolution). Thus, a tradeoff can be made between computational complexity (driven higher by using more origin points and cast rays/origin point as needed for higher spatial resolution) versus the spatial resolution of the HAIx probability map 12. Furthermore, it should be noted that the term "probability" in this context does not necessarily require a normalized probability. Rather, the spatially dependent infectious transmission probability given by the infectious transmission probability map 12 indicates relative likelihood of HAIx transmission, e.g. if a first location of the infectious transmission probability map 12 has a value that is, e.g. 50% higher than at a second location, this means that infectious transmission is more likely at the first location than at the second location, i.e. about 50% higher as indicated by the map 12.

Furthermore, an infectious transmission probability for a space or transport route of the medical facility floor map can be generated by aggregating the spatially dependent infectious transmission probability given by the infectious transmission probability map over the space or transport route.

In the illustrative examples, the infectious transmission probability map 12 is generated from densities of intersections of the cast rays over the medical facility floor map. However, the infectious transmission probability map can be generated from additional or other analysis of the intersections of rays cast over the medical facility floor map. For example, a measurement of integration can be employed. Integration is a normalized measure of distance from any a space of origin to all others in a system. In general, it calculates how close the origin space is to all other spaces, and can be seen as the measure of relative asymmetry (or relative depth). The measurement of integration can be computed for a central area of a room (or, more generally, a defined space) as the average (or other normalization) of distances along the rays cast from the room to intersections with other rays in each connecting room (or, or more generally, each other defined space). As another example, a choice metric can be employed. Choice measures, for a ray, the likelihood that the ray is passed through along all shortest routes from all spaces to all other spaces in the entire system or within a predetermined distance (radius) from each ray. For this approach, the choice metric for a designated ray passing along the center of a hall or other typical walking route is computed as the fraction of all other walking routes for which a ray passing along the other walking route intersects the designated ray. The various analyses, e.g. densities of intersections, measurements of integration, and/or choice metrics, can be combined as weighted averages or such in order to arrive at the HAIx probability map 12.

The HAIx probability map 12 can be a useful output by itself. For example, as shown in FIG. 2, in one useful implementation the medical facility floor map 50 is displayed at operation 82, and at operation 84 the HAIx probability map 12 is superimposed (or overlaid) onto the displayed medical facility floor map 50, for example by quantifying or coloring each pixel of the map 12 by the HAIx probability (as indicated by the number of cast ray intersections at the unit area containing that pixel). Such a display presentation may be reviewed by medical personnel to identify areas of the hospital having a high likelihood of infectious transmission so as to adjust patient transport routing, adjust cleaning schedules, or so forth.

Figure 3:
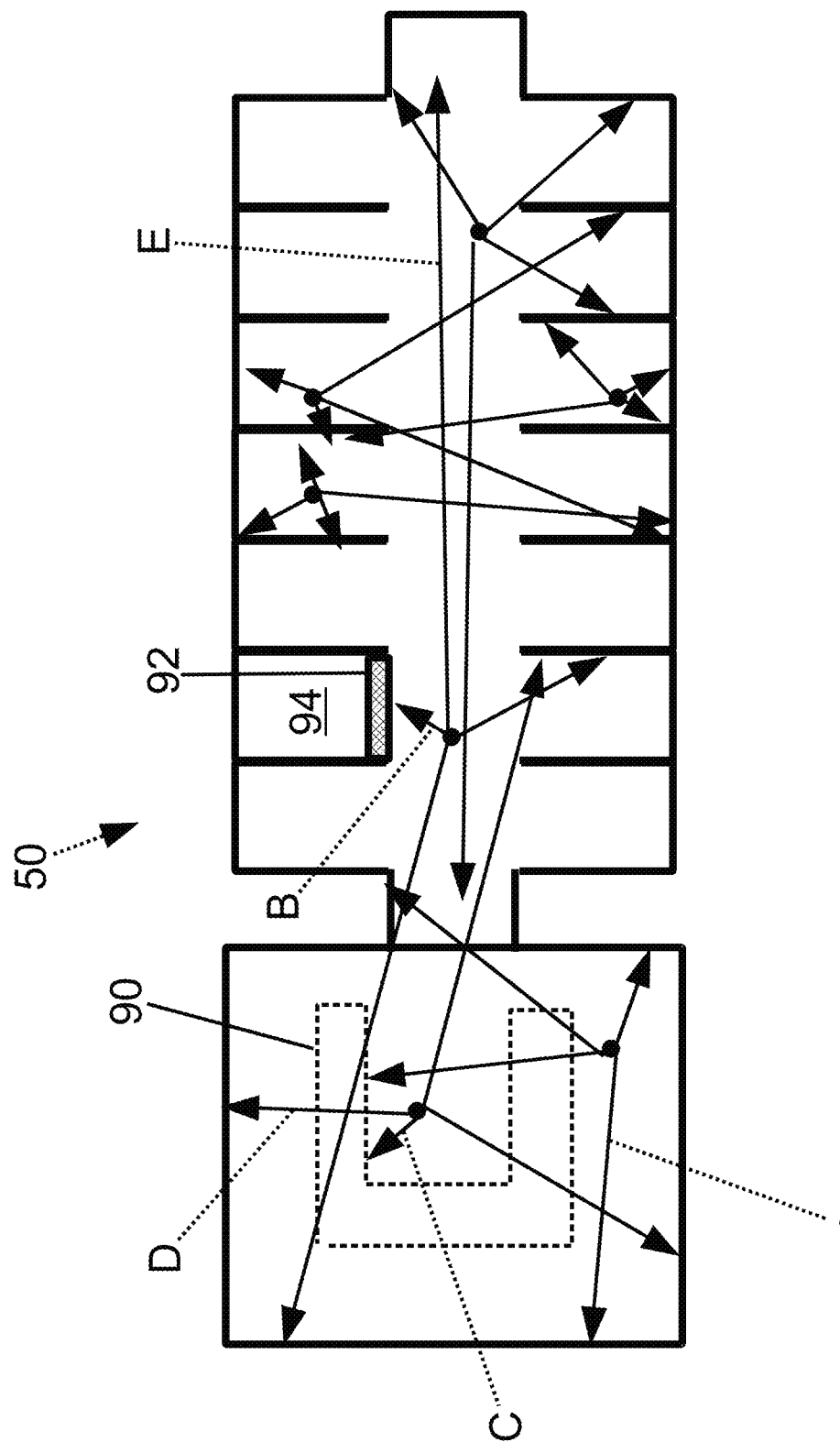
FIG. 3 diagrammatically shows the ray casting approach for estimating HAI transmission (HAIx) probability over the floor map.

With reference to FIG. 3, some illustrative ray casting situations are shown. In this example, the number of rays cast at each origin point is fixed at N=4, and only a few illustrative origin points are shown. (These values, N=4 and the illustrated number of origin points, are to be understood to be not sufficient to provide statistically significant number of cast ray intersections, but are merely shown in FIG. 3 to illustrate some ray casting situations). The medical facility floor map 50 is shown, including an illustrative porous barrier 90 (e.g., a nurses' station made up of desk space occupied by workstations and/or patient monitors, which present some barrier to travel but across which airborne or droplet-borne infectious transmission can occur), and one virtual barrier 92 (e.g. the doorway of an isolation room 94). Most rays, such as illustrative cast ray A, are stopped at physical barriers (e.g. walls) of the medical facility floor map 50. Similarly, a cast ray B is stopped at the virtual barrier 92. Cast ray C is a cast ray that is stopped at the porous barrier 90, whereas cast ray D is a cast ray that is not stopped at the porous barrier 90. Illustrative cast ray E is a ray that stops due to its reaching a maximum ray length (e.g. dictated by an infectious zone size in some embodiments) without intersecting any physical or virtual barriers.

Figure 4:
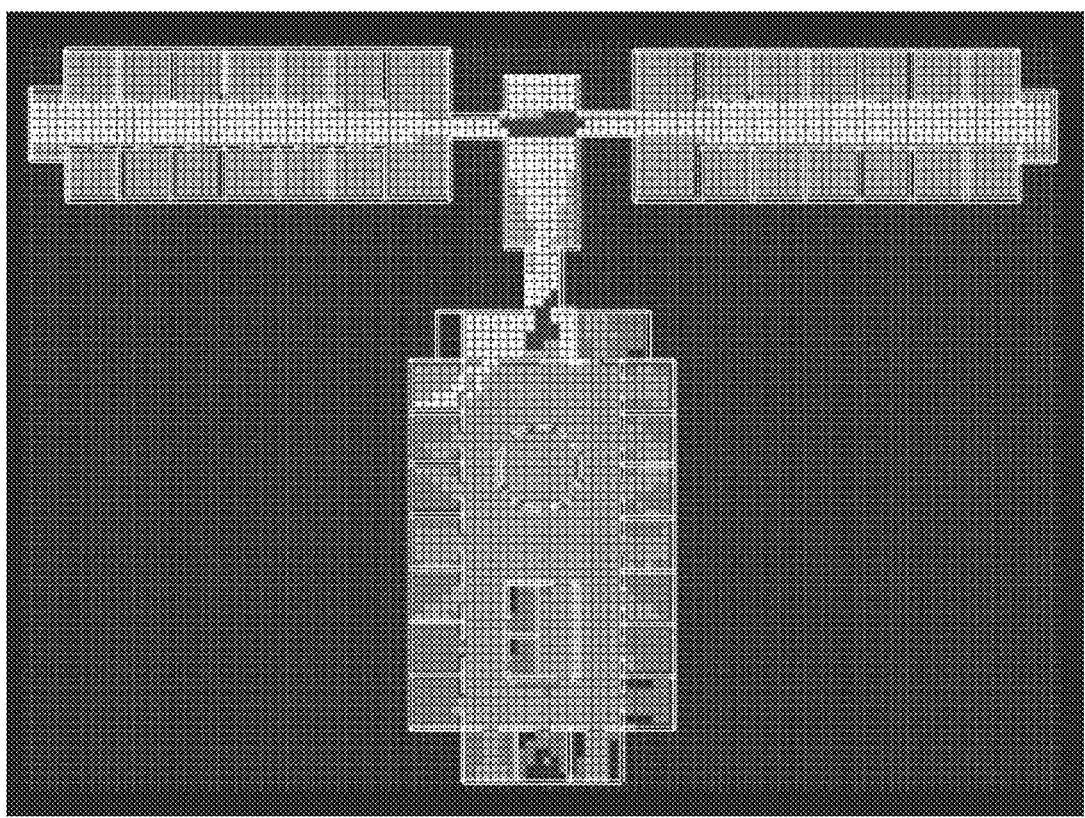
FIG. 4 diagrammatically shows an illustrative HAIx probability hospital floor map.

With reference to FIG. 4, a further example is shown of the HAIx probability map 12 which was generated by the ray casting approach of FIG. 2. In FIG. 4, pixels of higher HAIx probability are shown in lighter shade, while pixels of low HAIx probability are darker gray.

While the HAIx probability map 12 can be a useful output by itself, it may also be further processed and/or serve as an input to an application. In some embodiments, an infectious transmission probability for a space or transport route of the medical facility floor map 50 may be computed by aggregating the spatially dependent infectious transmission probability given by the infectious transmission probability map 12 over the space or transport route. For example, the infectious transmission probability for a route may be computed by summing the spatially dependent infectious transmission probabilities for all area units of the infectious transmission probability map 12 along the route and then dividing by the total number of area units along the route. Similarly, the infectious transmission probability for a space may be computed by summing the spatially dependent infectious transmission probabilities for all area units of the infectious transmission probability map 12 in the space and then dividing by the total number of area units in the space. In one presentation approach, the display 32 presents at least a portion of the medical facility floor map 50 overlaid with a graphic representing the space or transport route with the graphic labeled with the computed infectious transmission probability for a space or transport route. The graphic may, for example, employ a graphic comprising a shading and/or coloration of the space, with the infectious transmission probability labeled as a textual label. For a route, the graphic may be a line (optionally colored or shown as a dashed line or otherwise highlighted) labeled textually with the infectious transmission probability.

Figure 5:
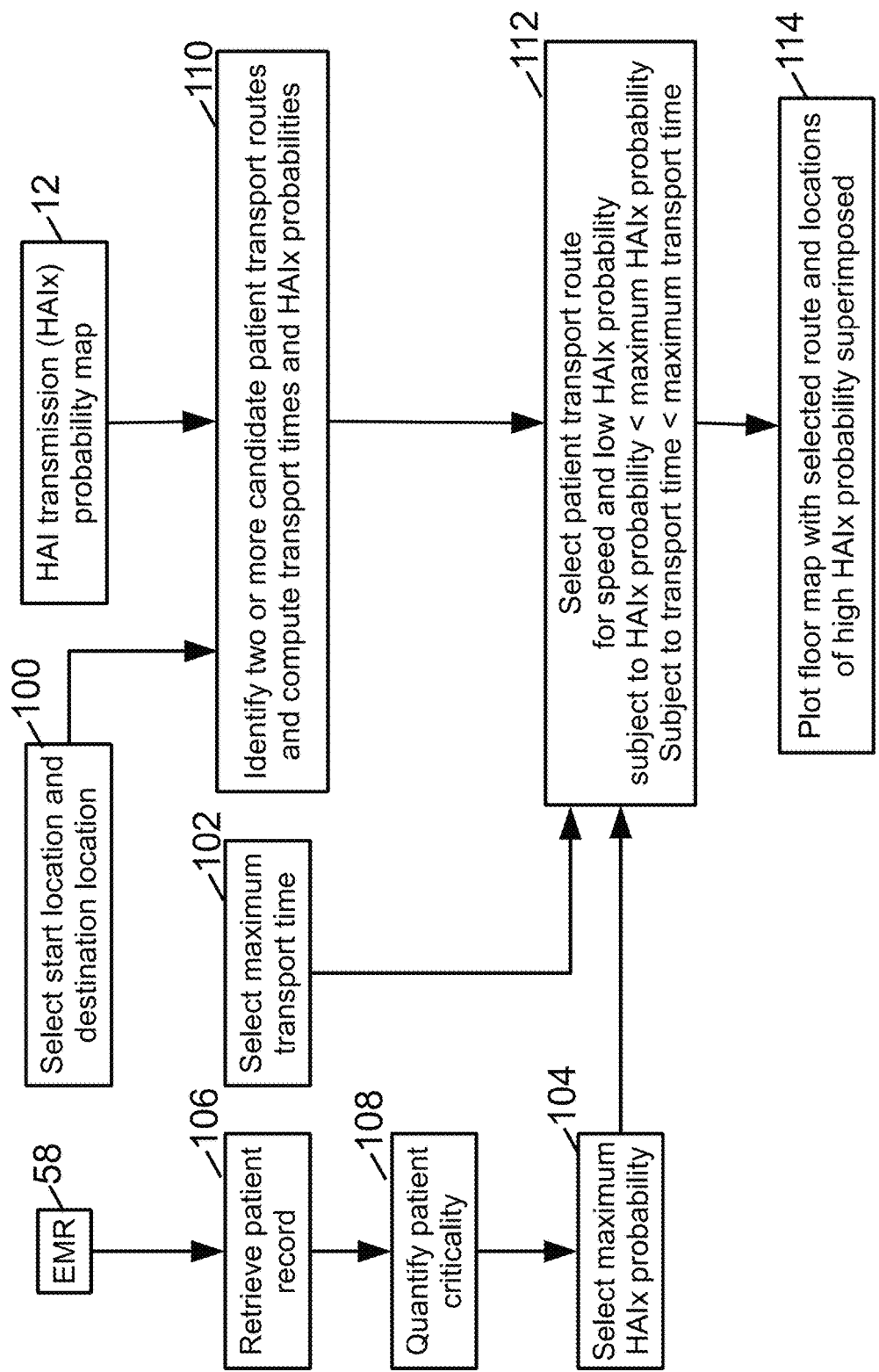
FIG. 5 diagrammatically shows operation of an illustrative embodiment of the patient transport router of FIG. 1.

With reference now to FIG. 5, an illustrative method suitably performed by the patient transport router 14 of FIG. 1 is described. The user identifies the start location and the destination location in an operation 100 both in the medical facility floor map 50, and optionally also identifies a maximum transport time in an operation 102. The maximum transport time may be chosen based on clinical considerations, workflow efficiency considerations, and/or so forth. A maximum transmission probability 104 may also be selected or determined. In illustrative FIG. 5, the maximum transmission probability 104 is determined for a specific patient by retrieving the patient record in an operation 106 from the EMR 58, quantifying patient criticality in an operation 108 on the basis of the retrieved patient record (e.g., based on the indicated diagnosed condition(s) of the patient, with a look-up table associating each condition with a corresponding criticality level), and selecting a maximum transmission probability 104 deemed acceptable for the patient's condition (e.g., again optionally using a look-up table associating patient criticality levels with corresponding maximum acceptable transmission probability values). In an operation 110, two or more candidate patient transport routes are identified for transporting a patient from the start location to the destination location. This may be done manually, i.e. by displaying the medical facility floor map 50 on a display and enabling a user to employ a mouse pointer, touch-sensitive display, or other user input device to draw one or more candidate routes. Alternatively, the operation 110 can be performed automatically by identifying contiguous paths connecting the start and destination locations. In an operation 112, one of the candidate patient transport routes is selected on the basis of chosen criterion at least one of which is based on the infectious transmission probabilities computed for the paths by aggregating the spatially dependent infectious transmission probability given by the infectious transmission probability map 12 over the candidate patient transport route. For example, this can be done by summing the spatially dependent infectious transmission probabilities for all area units of the infectious transmission probability map 12 along the candidate route and then dividing by the total number of area units along the route. In illustrative FIG. 5, the selection criteria optimize for transport speed and low HAIx probability, subject to the HAIx probability being less than the maximum transmission probability chosen at 104 and further subject to the transport time being less than the maximum transport time selected at 102. It will be appreciated that if, for example, transport time is not of concern then the selection criteria will suitably be based only on minimizing HAIx probability. In an operation 114, the medical facility floor map 50 is presented on a display with the selected patient transport route superimposed on the displayed map. Optionally, locations of high HAIx probability along the route are highlighted, e.g. using color coding as described previously (operation 84 of FIG. 2).

Figure 6:
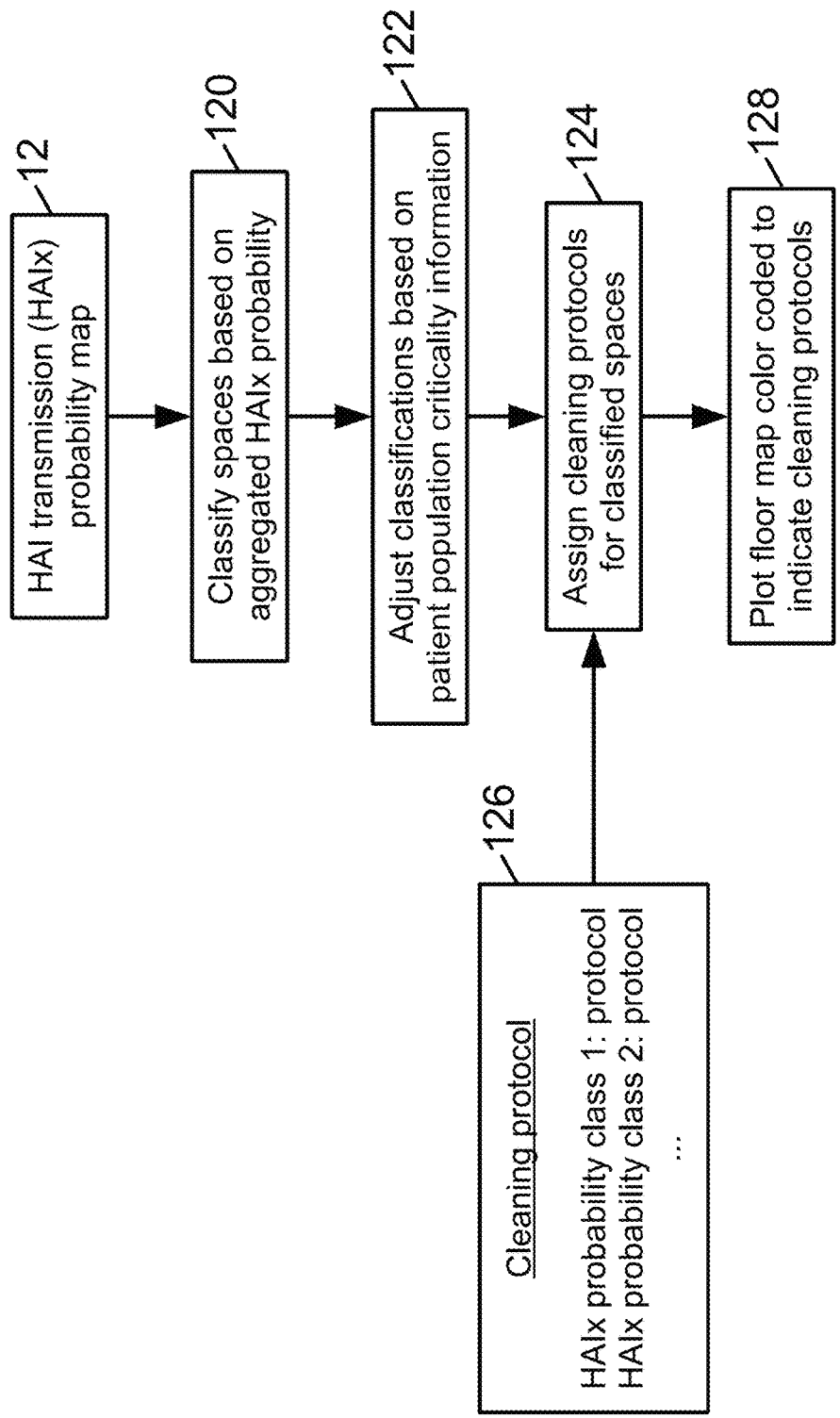
FIG. 6 diagrammatically shows operation of an illustrative embodiment of the hospital cleaning scheduler of FIG. 1.

With reference now to FIG. 6, an illustrative method suitably performed by the cleaning scheduler 16 of FIG. 1 is described. In an operation 120, each space of the medical facility floor map 50 is classified based on the infectious transmission probability for the space. The spaces, again, may for example be rooms, hallways, closets, or other suitably defined spaces. The infectious transmission probability for a space of the medical facility floor map 50 may be computed by aggregating the spatially dependent infectious transmission probability given by the infectious transmission probability map 12 over the space. For example, the infectious transmission probability for a space may be computed by summing the spatially dependent infectious transmission probabilities for all area units of the infectious transmission probability map 12 in the space and then dividing by the total number of area units in the space. Classification of the spaces may, for example, be based on these infectious transmission probabilities, optionally augmented by other metrics such as the peak infectious transmission probability anywhere in the space (i.e., the maximum value of the infectious transmission probability map 12 anywhere in the space). In an optional operation 122, the classifications of the spaces may be adjusted based on patient population criticality information. For example, recognizing that infectious transmission may be more likely (and have more serious consequences) in a critical care ward, classifications of such areas may be increased by a chosen factor at operation 122. (In other embodiments, this is partially or wholly taken into account by selecting the number of origin points and/or the number of rays cast per origin point based on this criticality information in the generation method described with reference to FIG. 2). In an operation 124, cleaning protocols are assigned for the various spaces based on their infectious probability classifications. For example, a look-up table 126 may specify a cleaning protocol for each space class, and hence the cleaning protocol that is assigned to a space is retrieved from the look-up table 126 for the class of that space. In an operation 128, the medical facility floor map 50 is displayed with the cleaning protocol information superimposed, e.g. indicated by color coding.

Figure 7:
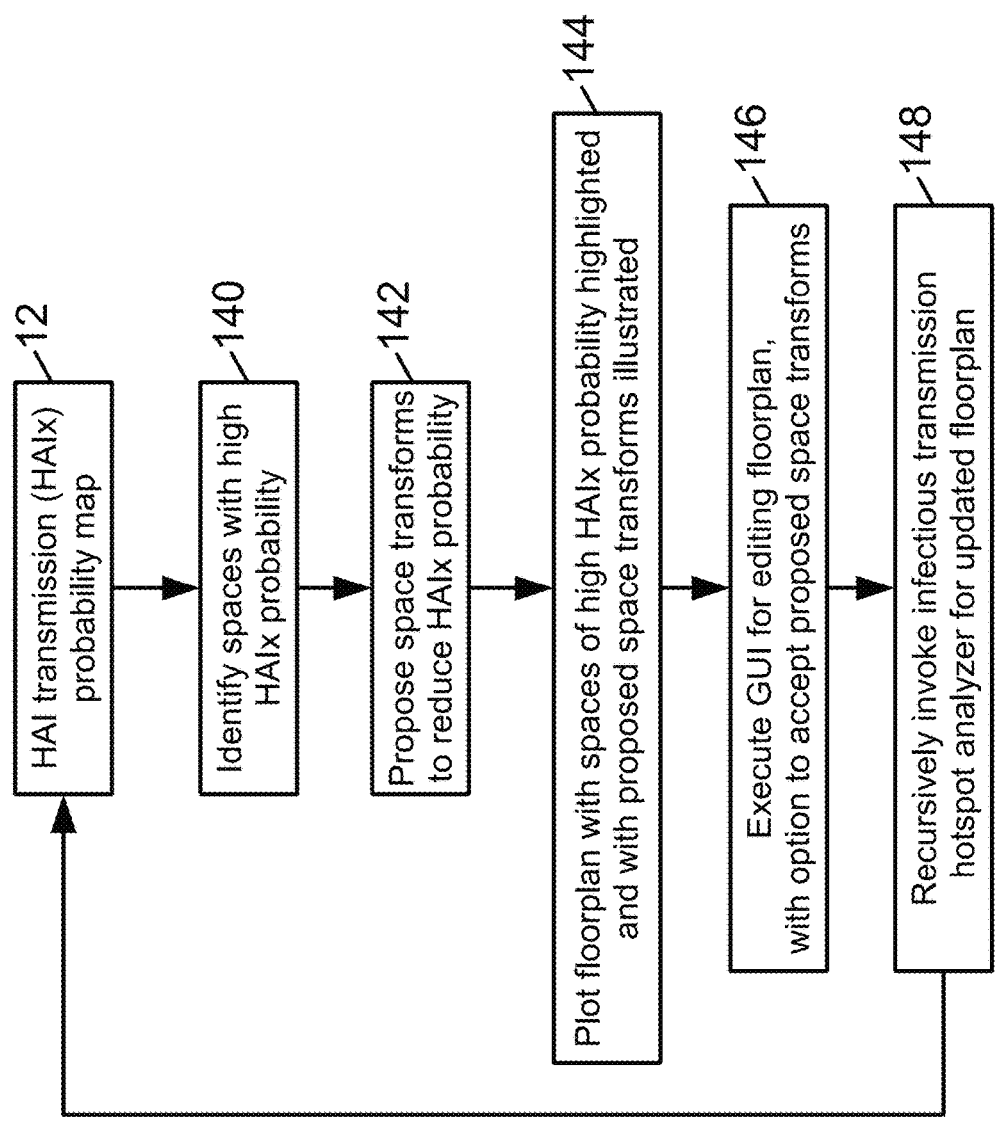
FIG. 7 diagrammatically shows operation of an illustrative embodiment of the hospital floorplan designer of FIG. 1.

With reference now to FIG. 7, an illustrative method suitably performed by the floorplan designer 18 of FIG. 1 is described. In an operation 140, spaces of the medical facility floor map 50 with high infectious transmission probability as indicated by the HAIx probability map 12 are identified. This may be by way of applying a threshold probability and identifying any area units whose HAIx probability exceeds this threshold, for example. In an operation 142, space transforms are proposed to reduce the HAIx probability at the identified areas. For example, an area of high HAIx probability along the center of a narrow hallway or corridor may be reduced by widening the hallway or corridor, or by adding an additional corridor to re-route some traffic off that problematic hallway or corridor. An unacceptably high HAIx probability in a room that connects with several other rooms or corridors may be reduced by omitting some of these connections (thereby trading off less flexible traffic routing for more isolation of that room). Other possible transforms may include adding barrier walls or so forth. In an operation 144, the floorplan is displayed with the areas of high HAIx probability highlighted and with the proposed space transforms illustrated, e.g. using dashed lines to indicate the proposed changes. In an operation 146, a graphical user interface (GUI) is executed to allow the user to edit the floorplan. Preferably, the GUI allows for the user to select a proposed space transform, e.g. by clicking on it to bring up a contextual menu that allows the user to select to accept the proposed space transform, upon which selection the transformed space replaces the original space in the floorplan rendering. When the user is satisfied with the modifications, a suitable user input is selected by the user (e.g., a "Done" button or user control) and in an operation 148 the infectious transmission hotspot analyzer 10 is invoked to analyze the updated floorplan to produce an updated HAIx probability map 12, and process flow returns to block 140.

The foregoing are some illustrative applications of the disclosed infectious transmission probability analyses. It will be appreciated that additional and/or other applications may be implemented, e.g. to optimize hospital staff ingress/egress to/from the medical facility, to optimize location of critical care wards, optimize authorized areas for access by visitors, and/or so forth.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium having stored thereon program code readable and executable by one or more electronic processors operatively connected with at least one display to perform operations including:
   selecting a number of ray origin points in response to a statistical occupancy of a medical facility floor map, a communicability of a specific disease being mapped, or a size of an infectious zone of the specific disease being mapped;
   selecting cast rays in response to the number of ray origin points, the cast rays stopping upon encountering a physical barrier mapped in the medical facility floor map;
   defining at least one physical barrier mapped in the medical facility floor map as a porous barrier, the cast rays stopping upon encountering the porous physical barrier with a stopping probability indicative of porosity of the porous physical barrier;
   generating an infectious transmission probability map from intersections of the cast rays over the medical facility floor map, wherein the transmission probability map is generated from densities of intersections of the cast rays over the medical facility floor map, the densities incorporating the porosity of the porous physical barrier; and
   displaying, on the at least one display, at least a portion of the medical facility floor map overlaid with the infectious transmission probability map, wherein the displayed at least a portion of the medical facility floor map is overlaid with infectious transmission probability by being quantified or color coded as defined by the infectious transmission probability map.

2. The non-transitory computer readable medium of claim 1 wherein the generating comprises:
   generating the infectious transmission probability map from the overall interaction of rays cast from each respective defined space via intersections with other rays in each other defined space.

3. The non-transitory computer readable medium of claim 1 wherein the generating comprises:
   generating the infectious transmission probability map from choice metrics wherein the choice metric for a designated ray passing along the center of a walking route is computed as the fraction of all other walking routes for which a ray passing along the other walking route intersects the designated ray.

4. The non-transitory computer readable medium of claim 1 wherein the operations further include defining, via at least one user input device operatively connected with the one or more electronic processors, a virtual barrier in the medical facility floor map, the cast rays further stopping upon encountering the virtual barrier.

5. The non-transitory computer readable medium of claim 1 wherein the operations further include receiving an infectious transmission zone size, the cast rays further stopping upon the cast ray reaching a length equal to the infectious transmission zone size.

6. The non-transitory computer readable medium of claim 1 wherein the operations further include receiving occupancy statistics for the medical facility, at least one of (i) the distribution of the ray origin points and (ii) a number of rays cast from each origin point being dependent on the occupancy statistics for the medical facility where the origin points reside.

7. The non-transitory computer readable medium of claim 1 wherein the operations further include receiving space classifications for spaces of the medical facility floor map, at least one of (i) the distribution of the ray origin points and (ii) a number of rays cast from each origin point being dependent on the space classifications of the spaces of the medical facility floor map in which the origin points reside.

8. The non-transitory computer readable medium of claim 1 wherein the operations further include:
for a start location and a destination location both defined in the medical facility floor map, identifying a plurality of candidate patient transport routes from the start location to the destination location;
for each candidate patient transport route, computing a patient transport time based at least on a length of the candidate patient transport route;
for each candidate patient transport route, computing an infectious transmission probability by aggregating the spatially dependent infectious transmission probability given by the infectious transmission probability map over the route;
selecting a patient transport route from the candidate patient transport routes based on the transport times and infectious transmission probabilities computed for the candidate patient transport routes; and
overlaying the patient transport route on the displayed at least a portion of the medical facility floor map.

9. The non-transitory computer readable medium of claim 1 wherein the operations further include:
classifying spaces of the medical facility floor map based on aggregation of the spatially dependent infectious transmission probability given by the infectious transmission probability map over the respective spaces;
assigning cleaning protocols to the spaces based on the classifications of the spaces; and
overlaying the cleaning protocols assigned to the spaces on the displayed at least a portion of the medical facility floor map.

10. The non-transitory computer readable medium of claim 1 wherein the operations further include:
computing infectious transmission probabilities for spaces of the medical facility floor map by aggregating the spatially dependent infectious transmission probability given by the infectious transmission probability map over the respective spaces;
identifying proposed space transforms to the medical facility floor map that would reduce the computed infectious transmission probabilities for the spaces; and
overlaying the proposed space transforms on the displayed at least a portion of the medical facility floor map.

11. The non-transitory computer readable medium of claim 1 wherein the rays are cast from the ray origin points at an eye level or at a knee level or at both an eye level and a knee level.

12. A method of epidemiology transmission probability analysis comprising:
selecting a number of ray origin points in response to a statistical occupancy of a medical facility floor map, a communicability of a specific disease being mapped, or a size of an infectious zone of the specific disease being mapped;
selecting cast rays in response to the number of ray origin points generated, the cast rays stopping upon encountering a physical barrier mapped in the medical facility floor map;
receiving a user input via a user input device operatively connected with the one or more electronic processors wherein the user input defines a porous barrier in the medical facility floor map, the cast rays further stopping upon encountering the porous barrier with a stopping probability indicative of porosity of the porous barrier;
generating an infectious transmission probability map from intersections of the cast rays, wherein the transmission probability map is generated from densities of intersections of the cast rays over the medical facility floor map, the densities incorporating the porosity of the porous physical barrier; and
displaying, on a display, at least a portion of the medical facility floor map overlaid with the infectious transmission probability map, wherein the displayed at least a portion of the medical facility floor map is overlaid with infectious transmission probability by being quantified or color coded as defined by the infectious transmission probability map;
wherein the distributing, the casting, and the computing are performed by one or more electronic processors.

13. The method of claim 12 wherein the generating comprises at least one of:
generating the infectious transmission probability map from the overall interaction of rays cast from each respective defined space via intersections with other rays in each other defined space; and
generating the infectious transmission probability map from choice metrics wherein the choice metric for a designated ray passing along the center of a walking route is computed as the fraction of all other walking routes for which a ray passing along the other walking route intersects the designated ray.

14. The method of claim 12 further comprising, receiving a user input via a user input device operatively connected with the one or more electronic processors wherein the user input defines a virtual barrier in the medical facility floor map, the cast rays further stopping upon encountering the virtual barrier.

15. The method of claim 12 wherein the cast rays further stop upon the cast ray reaching a length equal to an infectious transmission zone size.

16. The method of claim 12 wherein at least one of (i) the distribution of the ray origin points and (ii) a number of rays cast from each origin point is dependent on one of (I) occupancy statistics for the medical facility where the origin points reside or (II) space classifications for spaces of the medical facility floor map where the origin points reside.

17. The method of claim 12 further comprising:
for a start location and a destination location both defined in the medical facility floor map, identifying a plurality of candidate patient transport routes from the start location to the destination location;
for each candidate patient transport route, computing an infectious transmission probability by aggregating the spatially dependent infectious transmission probability given by the infectious transmission probability map over the route;

selecting a patient transport route from the candidate patient transport routes based on at least the infectious transmission probabilities computed for the candidate patient transport routes; and overlaying the patient transport route on the displayed at least a portion of the medical facility floor map.

18. The method of claim 12 further comprising:

classifying spaces of the medical facility floor map based on aggregation of the spatially dependent infectious transmission probability given by the infectious transmission probability map over the respective spaces;

assigning cleaning protocols to the spaces based on the classifications of the spaces; and overlaying the cleaning protocols assigned to the spaces on the displayed at least a portion of the medical facility floor map.

19. The method of claim 12 further comprising:

computing infectious transmission probabilities for spaces of the medical facility floor map by aggregating the spatially dependent infectious transmission probability given by the infectious transmission probability map over the respective spaces;

identifying proposed space transforms that would reduce the computed infectious transmission probabilities for the spaces; and overlaying the proposed space transforms on the displayed at least a portion of the medical facility floor map.

20. The method of claim 12, further comprising the step of adjusting a floorplan design based on the displayed portion of the medical facility floor map overlaid with the infectious transmission probability map.

21. The method of claim 12, further comprising the step of transporting a patient along a patient transport route selected from a plurality of candidate patient transport routes, wherein the selected patient transport route is selected based on the displayed portion of the medical facility floor map overlaid with the infectious transmission probability map.

22. An epidemiology transmission probability analysis device comprising:

at least one electronic processor;

at least one display operatively connected with the electronic processor; and at least one non-transitory storage medium storing a medical facility floor map and instructions readable and executable by the at least one electronic processor to perform operations including:

selecting a number of ray origin points in response to a statistical occupancy of a medical facility floor map, a communicability of a specific disease being mapped, or a size of an infectious zone of the specific disease being mapped;

selecting cast rays in response to the number of ray origin points generated, the cast rays stopping upon encountering a physical barrier mapped in the medical facility floor map;

receiving via a user input operatively connected with the one or more electronic processors, wherein the user input defines a porous barrier in the medical facility floor map, the cast rays further stopping upon encountering the porous barrier with a stopping probability indicative of porosity of the porous barrier;

generating an infectious transmission probability map from intersections of the cast rays, wherein the transmission probability map is generated from densities of intersections of the cast rays over the medical facility floor map, the densities incorporating the porosity of the porous physical barrier;

computing an infectious transmission probability for a space or transport route of the medical facility floor map by aggregating the spatially dependent infectious transmission probability given by the infectious transmission probability map over the space or transport route; and controlling the at least one display to present at least a portion of the medical facility floor map overlaid with a graphic representing the space or transport route with the graphic labeled with the computed infectious transmission probability for a space or transport route.

23. The epidemiology transmission probability analysis device of claim 22 wherein the generating comprises one or more of:

generating the infectious transmission probability map from densities of intersections of the cast rays over the medical facility floor map;

generating the infectious transmission probability map from the overall interaction of rays cast from each respective defined space via intersections with other rays in each other defined space; and generating the infectious transmission probability map from choice metrics wherein the choice metric for a designated ray passing along the center of a walking route is computed as the fraction of all other walking routes for which a ray passing along the other walking routes intersects the designated ray.

24. The epidemiology transmission probability analysis device of claim 22 wherein the cast rays further stop upon reaching a cast ray length equal to an infectious transmission zone size.

25. The epidemiology transmission probability analysis device of claim 22 wherein at least one of (i) the distribution of the ray origin points and (ii) a number of rays cast from each origin point is dependent on one of (I) occupancy statistics for the medical facility or (II) space classifications for spaces of the medical facility floor map.

26. The epidemiology transmission probability analysis device of claim 22 wherein the rays are cast from the ray origin points at an eye level or at a knee level or at both an eye level and a knee level.

* * * * *